(12) United States Patent (10) Patent No.: US 8,163,903 B2
Sallares Rosell et al. (45) Date of Patent: Apr. 24, 2012

(54) PROCESS FOR THE PREPARATION OF N-[5-(3-DIMETHYLAMINO-ACRYLOYL)-2-FLUORO-PHENYL]-N-METHYL-ACETAMIDE

(75) Inventors: Juan Sallares Rosell, Sant Cugat Del Vallès (ES); Francisco Marquillas, Barcelona (ES)

(73) Assignee: Interquim, S.A., Sant Cugat Del Valles (ES)

( * ) Notice: Subject to any disclaimer, the term of this patent is extended or adjusted under 35 U.S.C. 154(b) by 0 days.

(21) Appl. No.: 13/144,066

(22) PCT Filed: Jan. 11, 2010

(86) PCT No.: PCT/EP2010/050235
§ 371 (c)(1),
(2), (4) Date: Jul. 11, 2011

(87) PCT Pub. No.: WO2010/081788
PCT Pub. Date: Jul. 22, 2010

(65) Prior Publication Data
US 2011/0275809 A1 Nov. 10, 2011

(30) Foreign Application Priority Data
Jan. 13, 2009 (ES) .................. 200900089

(51) Int. Cl.
*C07D 487/04* (2006.01)
*C07C 233/88* (2006.01)
(52) U.S. Cl. ...................... 544/281; 564/218
(58) Field of Classification Search .......... 564/218; 544/281
See application file for complete search history.

(56) References Cited

U.S. PATENT DOCUMENTS
2005/0070555 A1 3/2005 Alonso-Alija et al.

FOREIGN PATENT DOCUMENTS
EP 1 736 475 A 12/2006

OTHER PUBLICATIONS
International Search Report, dated Jun. 8, 2010, issued in PCT/EP2010/050235.

*Primary Examiner* — Kamal Saeed
*Assistant Examiner* — Kristin Bianchi
(74) *Attorney, Agent, or Firm* — Birch, Stewart, Kolasch & Birch, LLP

(57) ABSTRACT

The present invention relates to a new process for the preparation of N-[5-(3-dimethylamino-acryloyl)-2-fluorophenyl]-N-methyl-acetamide (I) in a high yield and high purity, which is an intermediate in the synthesis of compounds with affinity for $GABA_4$ receptor. In this process, N-(5-acetyl-2-fluorophenyl)-N-methyl-acetamide (VI) is reacted with an excess of N,N-dimethylformamide dimethyl acetal (NNDMF-DMA). The present invention also provides a new process for the preparation of a compound with affinity for $GABA_4$ receptor, N-{2-fluoro-5-[3-(thiophene)-2-carbonyl-pyrazolo[1,5-a]pyrimidin-7-yl]phenyl}-N-methyl-acetamide (II), which comprises the following steps: a) methylation of N-(5-acetyl-2-fluorophenyl)-N-acetamide (IV) with a methyl sulfonate, b) reaction of the resulting compound (VI) with NNDMF-DMA, and c) reaction of the resulting compound (I) with (5-amino-1H-pirazol-4-yl)thiophen-2-yl-methanone (III) in glacial acetic acid. The present invention also relates to new intermediate (VI).

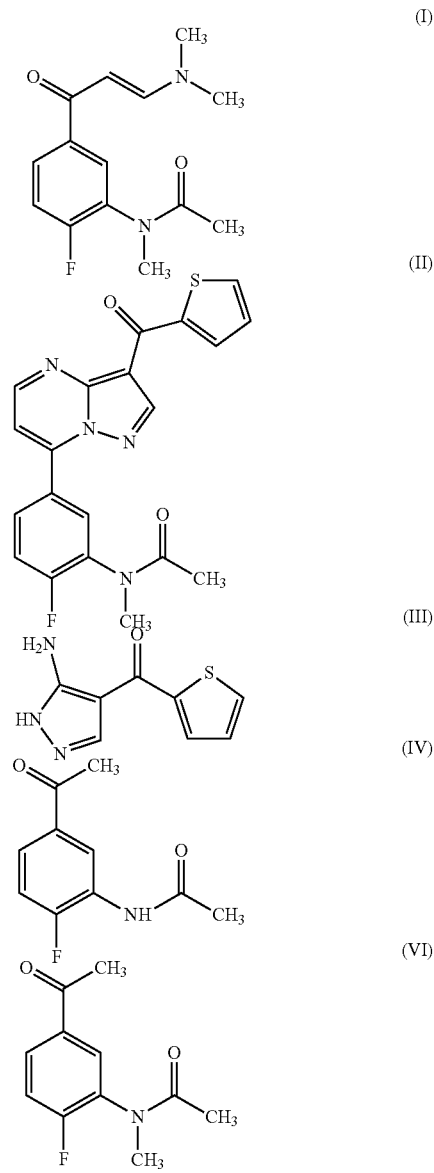

15 Claims, No Drawings

PROCESS FOR THE PREPARATION OF N-[5-(3-DIMETHYLAMINO-ACRYLOYL)-2-FLUORO-PHENYL]-N-METHYL-ACETAMIDE

FIELD OF THE INVENTION

The present invention relates to a new process for the preparation of N-[5-(3-dimethylamino-acryloyl)-2-fluoro-phenyl]-N-methyl-acetamide, which is useful as an intermediate in the preparation of pharmaceutical compounds.

BACKGROUND OF THE INVENTION

The compound of formula (I), N-[5-(3-dimethylamino-acryloyl)-2-fluoro-phenyl]-N-methyl-acetamide, is a key intermediate in the preparation of halogenated pyrazolo[1,5-a]pyrimidines with high affinity for $GABA_A$ receptor as described in Patent Application EP1736475A1.

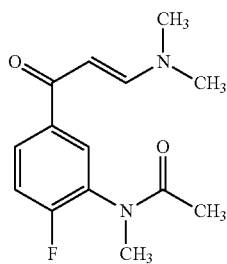

(I)

Compound (II), N-{2-fluoro-5-[3-(thiophene)-2-carbonyl-pyrazolo[1,5-a]pyrimidin-7-yl]phenyl}-N-methyl-acetamide, which was firstly described in the above patent application, is particularly useful for treating or preventing anxiety, epilepsy, sleep disorders, and insomnia, for inducing sedation-hypnosis, anesthesia, and muscle relaxation, and for modulating the necessary time to induce sleep and its duration.

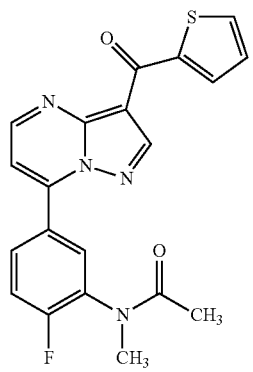

(II)

In the above patent application, final compound (II) is prepared by reacting (I)

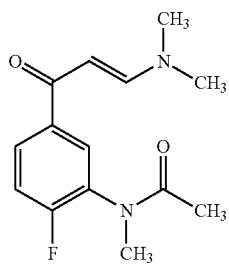

(I)

with (5-amino-1H-pyrazol-4-yl)thiophene-2-yl-methanone of formula (III)

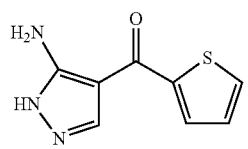

(III)

in glacial acetic acid. In turn, intermediate (I) is prepared in two steps from N-(5-acetyl-2-fluorophenyl)-N-acetamide of formula (IV)

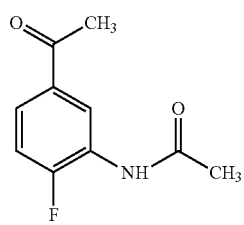

(IV)

which is treated with an excess of N,N-dimethylformamide dimethyl acetal (NNDMF-DMA) and subsequent N-methylation of the resulting compound, N-[5-(3-dimethylamino-acryloyl)-2-fluoro-phenyl]acetamide, of formula (V)

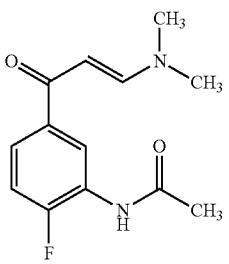

(V)

with methyl iodide in dimethylformamide (DMF) under an inert atmosphere at 0° C., and in the presence of sodium hydride (Preparative Example 1).

The use of hazardous reagents such as methyl iodide and sodium hydride, the special experimental conditions, as for the example the low temperature required (0° C.), and the convenience of operating under an inert atmosphere in step (V)→(I) make the process of Patent Application EP1736475A1 inadvisable for the industrial production of N-{2-fluoro-5-[3-(thiophene)-2-carbonyl-pyrazolo[1,5-a]pyrimidin-7-yl]phenyl}-N-methyl-acetamide (II). In addition, other disadvantages of this process are that key intermediate (I) from (IV) through (V) is obtained with a total yield of 40%, and HPLC purity is 94.9%.

There is, therefore, a need to provide a novel process for intermediate (I) that avoids the use of hazardous materials and truly proves to be efficient from an industrial viewpoint.

The inventors of the present invention have discovered a new process for the preparation of (I) which is more eco-friendly and easily industrializable than current methods and affords the product in high yield and purity.

OBJECT OF THE INVENTION

It is an object of the invention to provide a novel easily industrializable and environmentally friendly process for the preparation of N-[5-(3-dimethylamino-acryloyl)-2-fluoro-phenyl]-N-methyl-acetamide (I) which is obtained in a good yield and with adequate purity.

It is also an object of the invention to provide a novel process for the preparation of N-{2-fluoro-5-[3-(thiophene)-2-carbonyl-pyrazolo[1,5-a]pyrimidin-7-yl]phenyl}-N-methyl-acetamide (II).

Another object of the invention is to provide the new intermediate N-(5-acetyl-2-fluorophenyl)-N-methyl-acetamide (VI).

DETAILED DESCRIPTION OF THE INVENTION

The process for the preparation of N-[5-(3-dimethylamino-acryloyl)-2-fluoro-phenyl]-N-methyl-acetamide (I) according to the present invention comprises reacting the compound of formula (VI)

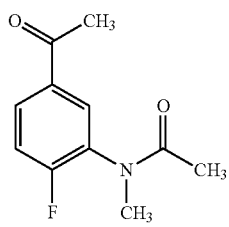

(VI)

with an excess of NNDMF-DMA in a proportion of 1.5-2.5 moles of NNDMF-DMA per mole of compound (VI) under reflux, followed by addition of an apolar aromatic solvent selected from the group consisting of toluene, o-xylene, m-xylene, p-xylene, ethylbenzene, styrene and cumene, and the mixtures thereof, at a temperature ranging from 70 to 90° C., and then an apolar aliphatic solvent selected from the group consisting of n-hexane, n-heptane, n-octane, 2,5-dimethylhexane, cyclohexane, methylcyclohexane, and the mixtures thereof, at the same temperature.

In a preferred embodiment, the proportion of NNDMF-DMA is 2 moles per mole of compound (VI).

In other preferred embodiments, toluene is chosen as an apolar aromatic solvent, the reaction temperature is 80° C. and the apolar aliphatic solvent is n-heptane.

In another preferred embodiment of the present invention, compound (VI) is obtained by a process comprising reacting the compound of formula (IV)

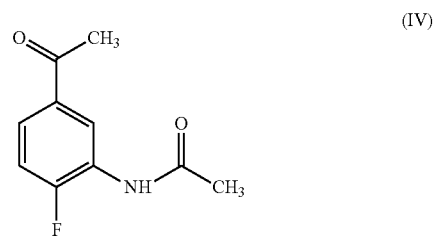

(IV)

with a methylating agent selected from the group consisting of methyl p-toluenesulfonate, methyl o-nitrobenzenesulfonate, methyl m-nitrobenzenesulfonate, methyl p-nitrobenzenesulfonate and methyl methanesulfonate, in a polar aprotic solvent selected from the group consisting of acetonitrile, benzonitrile, dimethylformamide, dimethylsulfoxide, dioxane, N-methyl-2-pyrrolidone, propionitrile and tetrahydrofurane, and the mixtures thereof, followed by neutralization with a basic agent selected from the group consisting of sodium hydroxide, potassium hydroxide, calcium hydroxide, sodium carbonate, potassium carbonate, calcium carbonate, sodium bicarbonate, potassium bicarbonate and calcium bicarbonate.

The methylation reaction is carried out by adding the basic agent at a temperature of 10-50° C. in a proportion from 1.0 to 1.5 moles in relation to substrate (IV), in the presence of the methylating agent which is in a proportion from 1.0 to 1.5 moles in relation to substrate (IV).

In other preferred embodiments, the reaction temperature is 30° C., the methylating agent selected is methyl p-toluenesulfonate which is employed in a proportion of 1.1 moles per mole of compound (IV), the polar aprotic solvent is acetonitrile, the basic agent is sodium hydroxide which is employed in a proportion of 1.1 moles per mole of compound (IV) and added after addition of the methylating agent.

A second object of the invention is to provide a process for the preparation of N-{2-fluoro-5-[3-(thiophene)-2-carbonyl-pyrazolo[1,5-a]pyrimidin-7-yl]phenyl}-N-methyl-acetamide (II)

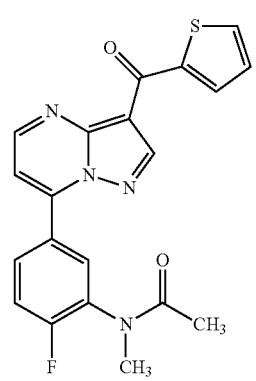

(II)

comprising the following steps:

a) reacting the compound of formula (IV)

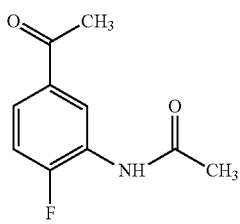

(IV)

with a methylating agent selected from the group consisting of methyl p-toluenesulfonate, methyl o-nitrobenzenesulfonate, methyl m-nitrobenzenesulfonate, methyl p-nitrobenzenesulfonate and methyl methansulfonate, in a proportion from 1.0 to 1.5 moles in relation to substrate (IV), at a temperature of 10-50° C., in a polar aprotic solvent selected from the group consisting of acetonitrile, benzonitrile, dimethylformamide, dimethylsulfoxide, dioxane, N-methyl-2-pyrrolidone, propionitrile and tetrahydrofurane, and the mixtures thereof, followed by neutralization with a basic agent selected from the group consisting of sodium hydroxide, potassium hydroxide, calcium hydroxide, sodium carbonate, potassium carbonate, calcium carbonate, sodium bicarbonate, potassium bicarbonate and calcium bicarbonate, in a proportion from 1.0 to 1.5 moles in relation to substrate (IV);

b) reacting the resulting compound of formula (VI)

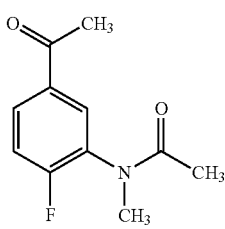

(VI)

with an excess of NNDMF-DMA in a proportion of 1.5-2.5 moles of NNDMF-DMA per mole of compound (VI) under reflux, followed by addition of an apolar aromatic solvent selected from the group consisting of toluene, o-xylene, m-xylene, p-xylene, ethylbenzene, styrene and cumene, and the mixtures thereof, at a temperature ranging from 70 to 90° C., and then an apolar aliphatic solvent selected from group consisting of n-hexane, n-heptane, n-octane, 2,5-dimethylhexane, cyclohexane, methylcyclohexane, and the mixtures thereof, at the same temperature; and c) reacting the resulting compound of formula (I)

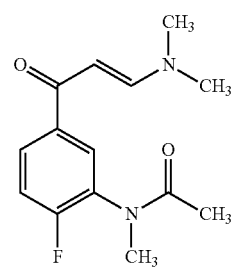

(I)

with the compound of formula (III)

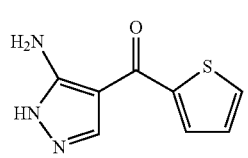

(III)

in glacial acetic acid at a temperature ranging from 60 to 90° C. over a period of 2-6 hours, and addition of an aliphatic alcohol selected from the group consisting of isopropanol, ethanol, n-propanol and methanol.

In a preferred embodiment of the second object of the invention, the following options are selected:

(i) in step a) firstly add methyl p-toluenesulfonate as methylating agent, in a proportion of 1.1 moles per mole of compound (IV), at a temperature of 30° C., in acetonitrile medium as a polar aprotic solvent, and then add sodium hydroxide as a basic agent, in a proportion of 1.1 moles per mole of compound (IV);

(ii) in step b) the proportion of 2 moles of NNDMF-DMA per mole of compound (VI), toluene as an apolar aromatic solvent, the temperature of 80° C., and n-heptane as an apolar aliphatic solvent; and (iii) in step c) the temperature of 75° C., the time period of 4 hours, and isopropanol as an aliphatic alcohol.

The present inventors have surprisingly found that the combination of a simple permutation in the order of reactions that lead to (I) from (IV) through (VI), instead of obtaining (I) from (IV) through (V) as described in the Preparative Example 1 of Patent Application EP1736475A1, the subsequent use of a methyl sulfonate as a methylating agent, preferably methyl p-toluenesulfonate, instead of methyl iodide as described in the aforesaid Preparative Example 1, the use of a weak base (alkali or earth-alkaline bicarbonate, carbonate, or hydroxide) instead of an alkaline hydride as described in the aforesaid Preparative Example 1, and the addition of said base subsequently to the addition of the methylating agent jointly shows the advantages of a total high yield (83%) and a high HPLC purity (99.7%) of compound (I).

The high purity attained by this new process is based, apart from the fact that methylation is performed on the ketone compound (IV) which is more stable than the enamine compound (V) from the process of Patent Application EP1736475A1, on the fact that methylation conditions can prevent the formation of an unstable anion from the acetamide group and the nucleophile substitution of the fluorine atom of compound (IV) can be minimized.

Moreover, the changes introduced hereby avoid using both hazardous reagents that can cause harm to people and to the environment and special operating conditions, especially, as far as temperature and inert atmosphere is concerned. The resultant process is, therefore, remarkably advantageous since a more efficient and safe production is afforded.

The advantages of the present invention over Patent Application EP1736475A1 are presented in Table 1.

TABLE 1

Comparative data in the preparation of key intermediate (I)

|  | EP1736475A1 (IV) → (V) → (I) | | Present invention (IV) → (VI) → (I) | |
| --- | --- | --- | --- | --- |
|  | Preparative Example 1 | | Example 1 | Example 2 |
| Reactions | (IV) → (V) | (V) → (I) | (IV) → (VI) | (VI) → (I) |
| Reagents | NNDMF-DMA | NaH/ICH₃ | methyl p-toluenesulfonate/NaOH | NNDMF-DMA |
| Solvents |  | DMF | acetonitrile | NNDMF-DMA / toluene/n-heptane |
| Experimental conditions | reflux 6.5 h | 0° C., inert atmosphere 5.5 h | 15-30° C. 15 h | reflux 8 h / 80-15° C. ≈2 h |
| Total yield (I) | 40% | | 83% | |
| Purity (I) | 94.9% | | 99.7% | |

A third object of the present invention is to provide the new intermediate compound, N-(5-acetyl-2-fluorophenyl)-N-methyl-acetamide, of formula (VI)

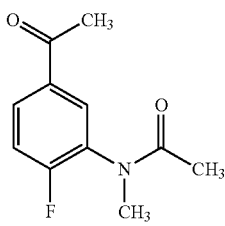

(VI)

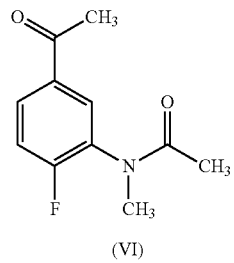

(VI)

In 800 mL of acetonitrile, 80 g (0.41 moles) of N-(5-acetyl-2-fluorophenyl)-N-acetamide (IV) (US2005070555) and 83.77 g (0.45 moles) of methyl p-toluenesulfonate were dissolved. The resulting mixture was cooled to 15-20° C. and 18.00 g (0.45 moles) of sodium hydroxide were added. Then the mixture was heated at 30° C. and kept under stirring for 15 h. Thin-layer chromatography (ethyl acetate: n-heptane 70:30) revealed the completeness of reaction. The mixture was cooled to 15-20° C. and 400 mL of water were added. Acetonitrile was mostly distilled under reduced pressure, and the resulting aqueous solution was extracted with methylene chloride (2×400 mL). The organic extracts were gathered and firstly wash with 400 mL of 5% sodium bicarbonate aqueous solution and then with 2×400 mL of water. The mixture was concentrated to nearly dryness under reduced pressure, and the resulting crude product was crystallized by dissolving at 50° C. with a mixture of 48 mL of toluene and 282 mL of n-heptane and slowly cooling to 15° C. The solid formed was filtered off, washed with a cold mixture (10-15° C.) of 40 mL of toluene and 248 mL of n-heptane, and then dried under vacuum at 30° C. A white solid (78 g, 91% yield) with a melting point=75.5-76.5° C. was obtained.

MS (ES) m/z=210 (MH+)
$^1$H NMR (400 MHz, Cl₃CD): δ 1.81 (3H, s), 2.55 (3H, s), 3.17 (3H, s), 7.23 (1H, t, J=8.4 Hz), 7.83 (1H, dd, J'=7.6 Hz, J'=2.4 Hz), 7.90 (1H, m).
HPLC=99.9%

EXAMPLES

Example 1

Synthesis of N-(5-acetyl-2-fluorophenyl)-N-methyl-acetamide (VI)

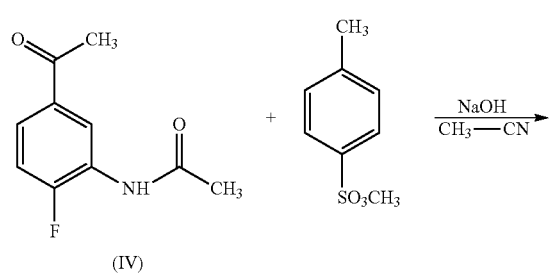

(IV)

Example 2

Synthesis of N-[5-(3-dimethylamino-acryloyl)-2-fluoro-phenyl]-N-methyl-acetamide (I)

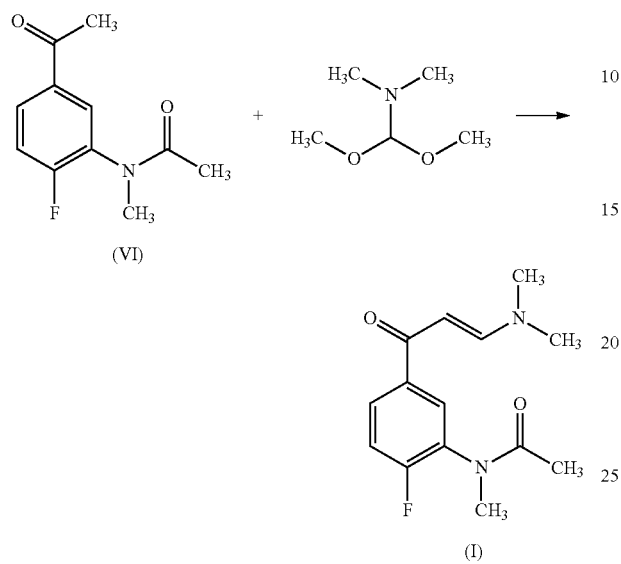

75.0 g (0.36 moles) of N-(5-acetyl-2-fluorophenyl)-N-methyl-acetamide (VI) were dissolved in 96.3 mL (86.4 g, 0.72 moles) of NNDMF-DMA. The resulting solution was refluxed for 8 hours. At the temperature of 80° C., 400 mL of toluene were added, and then, at the same temperature, 400 mL of n-heptane were slowly added. The resulting solution was slowly cooled to 15-20° C. The white-yellowish solid obtained by recrystallization was filtered off, washed with 263 mL of toluene:n-heptane (1:1), and then dried under vacuum at 40° C. A white-yellowish solid (84.1 g, 91.7% yield) with a melting point=131-132° C. was obtained.

MS (ES) m/z=265 (MH+)

$^1$H NMR (400 MHz, Cl$_3$CD): δ 1.81 (3H, s), 2.90 (3H, s), 3.10 (3H, s), 3.20 (3H, s), 5.57 81H, d, J=12 Hz), 7.14 (1H, t, J=8.8 Hz), 7.74-7.85 (3H, m).

HPLC=99.7%

Example 3

Synthesis of N-{2-fluoro-5-[3-(thiophene)-2-carbonyl-pyrazolo[1,5-a]pyrimidin-7-yl]phenyl}-N-methyl-acetamide (II)

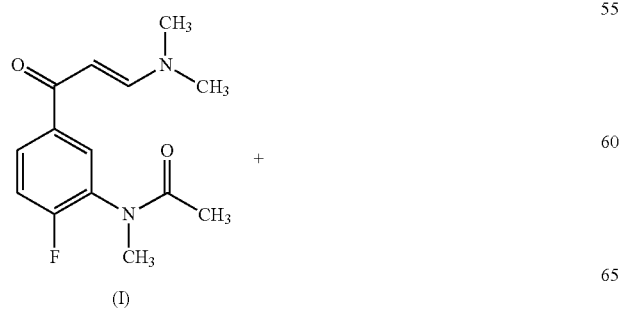

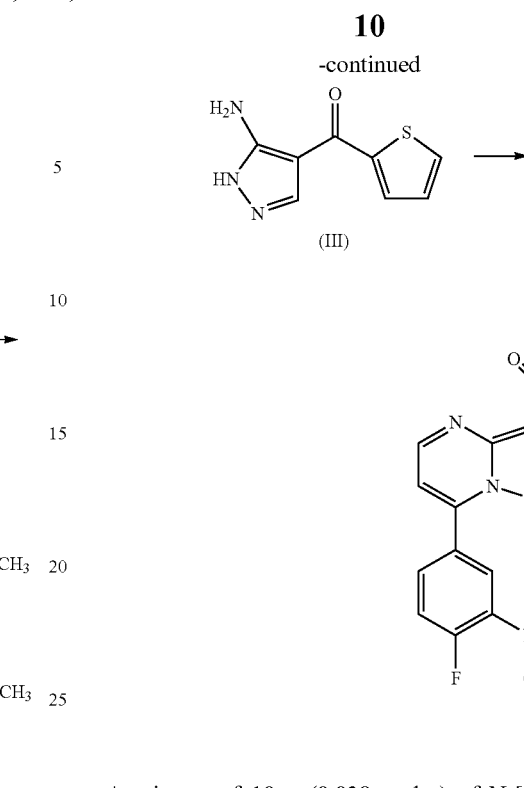

A mixture of 10 g (0.038 moles) of N-[5-(3-dimethylamino-acryloyl)-2-fluoro-phenyl]-N-methyl-acetamide (I) and 9.6 g (0.038 moles) of (5-amino-1H-pyrazol-4-yl) thiophene-2-yl-methanone (III) in 30 mL of glacial acetic acid was heated at 75° C. for 4 hours. Then, 30 mL of isopropanol were added and the precipitated solid was filtered off, washed with 90 mL of isopropanol, and dried under vacuum at 40° C. A white-yellowish solid (12.9 g, 86.5% yield) with a melting point=158-159° C. was obtained.

MS (ES) m/z=395 (MH+)

$^1$H NMR (400 MHz, Cl$_3$CD): δ 1.92 (3H, s), 3.24 (3H, s), 7.09 (1H, d, J=4.4 Hz), 7.12-7.14 (1H, m), 7.36 (1H, t, J=8.8 Hz), 7.64 (1H, d, J=4.8 Hz), 7.97-8.01 (2H, m), 8.07 (1H, dd, J=2.0 Hz, J=7.6 Hz), 8.64 (1H, s), 8.75 (1H, d, J=4 Hz).

HPLC=99.7%

The invention claimed is:

1. A process for the preparation of N-[5-(3-dimethylamino-acryloyl)-2-fluoro-phenyl]-N-methyl-acetamide of formula (I)

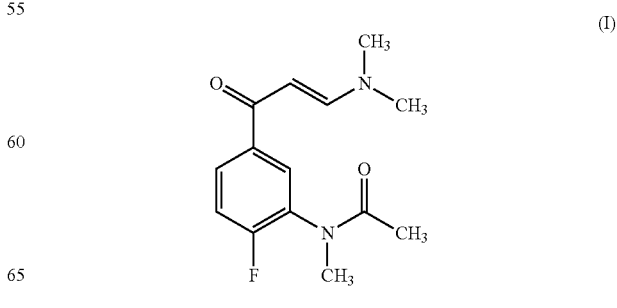

comprising reacting the compound of formula (VI)

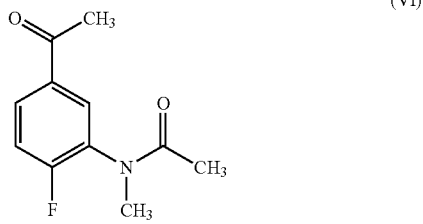

with an excess of N,N-dimethylformamide dimethyl acetal (NNDMF-DMA) in a proportion of 1.5-2.5 moles of NNDMF-DMA per mole of compound (VI) under reflux, followed by addition of an apolar aromatic solvent selected from the group consisting of toluene, o-xylene, m-xylene, p-xylene, ethylbenzene, styrene and cumene, and the mixtures thereof, at a temperature ranging from 70 to 90° C., and then an apolar aliphatic solvent selected from the group consisting of n-hexane, n-heptane, n-octane, 2,5-dimethylhexane, cyclohexane, methylcyclohexane, and the mixtures thereof, at the same temperature.

2. The process of claim 1, wherein the proportion of NNDMF-DMA is 2 moles per mole of compound (VI).

3. The process of claim 1, wherein the apolar aromatic solvent is toluene.

4. The process of claim 1, wherein the temperature is 80° C.

5. The process of claim 1, wherein the apolar aliphatic solvent is n-heptane.

6. The process of claim 1, wherein the compound of formula (VI) is obtained by a process which comprises reacting the compound of formula (IV)

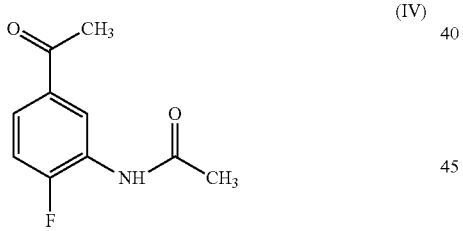

with a methylating agent selected from the group consisting of methyl p-toluenesulfonate, methyl o-nitrobenzenesulfonate, methyl m-nitrobenzenesulfonate, methyl p-nitrobenzenesulfonate and methyl methanesulfonate, in a polar aprotic solvent selected from the group consisting of acetonitrile, benzonitrile, dimethylformamide, dimethylsulfoxide, dioxane, N-methyl-2-pyrrolidone, propionitrile and tetrahydrofurane, and the mixtures thereof, in a proportion of 1.0 to 1.5 moles of methylating agent per mole of compound (IV), at a temperature of 15-50° C., followed by neutralization at the same temperature with a basic agent selected from the group consisting of sodium hydroxide, potassium hydroxide, calcium hydroxide, sodium carbonate, potassium carbonate, calcium carbonate, sodium bicarbonate, potassium bicarbonate and calcium bicarbonate, in a proportion from 1.0 to 1.5 moles of basic agent per mole of compound (IV).

7. The process of claim 6, wherein the methylating agent is methyl p-toluenesulfonate.

8. The process of claim 6, wherein the proportion of methyl p-toluenesulfonate is 1.1 moles per mole of compound (IV).

9. The process of claim 6, wherein the polar aprotic solvent is acetonitrile.

10. The process of claim 6, wherein the basic agent is sodium hydroxide.

11. The process of claim 6, wherein the proportion of sodium hydroxide is 1.1 moles per mole of compound (IV).

12. The process of claim 6, wherein the temperature is 30° C.

13. A process for the preparation of N-{2-fluoro-5-[3-(thiophene)-2-carbonyl-pyrazolo[1,5-a]pyrimidin-7-yl]phenyl}-N-methyl-acetamide (II)

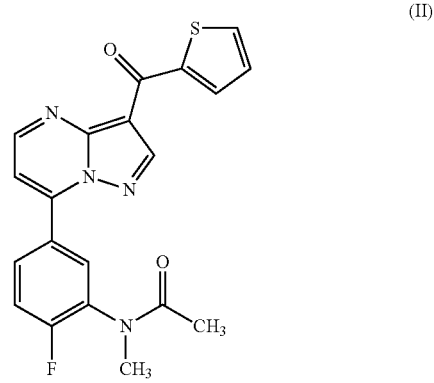

comprising the following steps:
a) reacting the compound of formula (IV)

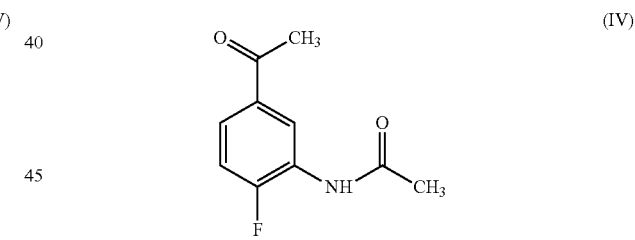

with a methylating agent selected from the group consisting of methyl p-toluenesulfonate, methyl o-nitrobenzenesulfonate, methyl m-nitrobenzenesulfonate, methyl p-nitrobenzenesulfonate and methyl methanesulfonate, in a polar aprotic solvent selected from the group consisting of acetonitrile, benzonitrile, dimethylformamide, dimethylsulfoxide, dioxane, N-methyl-2-pyrrolidone, propionitrile and tetrahydrofurane, and the mixtures thereof, in a proportion from 1.0 to 1.5 moles of methylating agent per mole of compound (IV), at a temperature of 10-50° C., followed by neutralization at the same temperature with a basic agent selected from the group consisting of sodium hydroxide, potassium hydroxide, calcium hydroxide, sodium carbonate, potassium carbonate, calcium carbonate, sodium bicarbonate, potassium bicarbonate and calcium bicarbonate, in a proportion from 1.0 to 1.5 moles of basic agent per mole of compound (IV);

b) reacting the resulting compound of formula (VI)

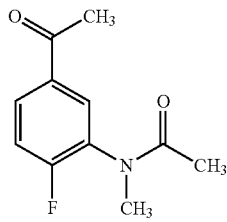
(VI)

with an excess of NNDMF-DMA in a proportion of 1.5-2.5 moles of NNDMF-DMA per mole of compound (VI) under reflux, followed by addition of an apolar aromatic solvent selected from the group consisting of toluene, o-xylene, m-xylene, p-xylene, ethylbenzene, styrene and cumene, and the mixtures thereof, at a temperature ranging from 70 to 90° C., and then an apolar aliphatic solvent selected from the group consisting of n-hexane, n-heptane, n-octane, 2,5-dimethylhexane, cyclohexane, methylcyclohexane, and the mixtures thereof, at the same temperature; and c) reacting the resulting compound of formula (I)

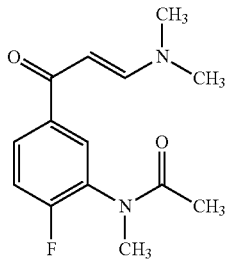
(I)

with the compound of formula (III)

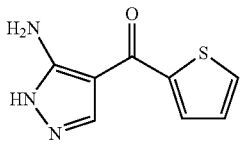
(III)

in glacial acetic acid at a temperature ranging from 60 to 90° C. over a period of 2-6 hours, and addition of an aliphatic alcohol selected from the group consisting of isopropanol, ethanol, n-propanol and methanol.

14. The process of claim 13, wherein
(i) in step a) the methylating agent is methyl p-toluenesulfonate in a proportion of 1.1 moles per mole of compound (IV), the polar aprotic solvent is acetonitrile, the temperature is 30° C., and the basic agent is sodium hydroxide in a proportion of 1.1 moles per mole of compound (IV);
(ii) in step b) the proportion of NNDMF-DMA is 2 moles per mole of compound (VI), the apolar aromatic solvent is toluene, the temperature is 80° C., and the apolar aliphatic solvent is n-heptane; and
(iii) in step c) the temperature is 75° C., the time period is 4 hours, and the aliphatic alcohol is isopropanol.

15. Compound N-(5-acetyl-2-fluorophenyl)-N-methyl-acetamide of formula (VI)

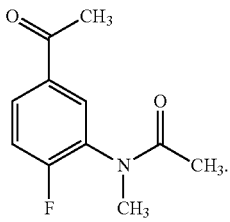
(VI)

* * * * *